US012653373B2

(12) United States Patent
Sakurai

(10) Patent No.: US 12,653,373 B2
(45) Date of Patent: Jun. 16, 2026

(54) CONTROL APPARATUS, MEDICAL SYSTEM AND METHOD FOR OPERATING MEDICAL SYSTEM

(71) Applicant: OLYMPUS MEDICAL SYSTEMS CORP., Tokyo (JP)

(72) Inventor: Ryosuke Sakurai, Tachikawa (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 314 days.

(21) Appl. No.: 18/367,795

(22) Filed: Sep. 13, 2023

(65) Prior Publication Data

US 2023/0414063 A1 Dec. 28, 2023

Related U.S. Application Data

(63) Continuation of application No. PCT/JP2021/011256, filed on Mar. 18, 2021.

(51) Int. Cl.
| | |
|---|---|
| *A61B 1/00* | (2006.01) |
| *H04B 7/06* | (2006.01) |
| *H04B 7/08* | (2006.01) |

(52) U.S. Cl.
CPC ...... *A61B 1/00006* (2013.01); *A61B 1/00009* (2013.01); *A61B 1/00016* (2013.01);
(Continued)

(58) Field of Classification Search
None
See application file for complete search history.

(56) References Cited

U.S. PATENT DOCUMENTS

| | | | | |
|---|---|---|---|---|
| 8,874,047 B2 * | 10/2014 | Alrabadi | ................ | H04B 1/525 |
| | | | | 455/66.1 |
| 2009/0247828 A1 * | 10/2009 | Watanabe | .......... | A61B 1/00066 |
| | | | | 600/131 |

(Continued)

FOREIGN PATENT DOCUMENTS

| | | | | | |
|---|---|---|---|---|---|
| CN | 104937853 A | * | 9/2015 | ......... | H04L 27/2626 |
| JP | 2005218704 A | * | 8/2005 | | |

(Continued)

OTHER PUBLICATIONS

International Search Report dated Jun. 15, 2021 received in PCT/JP2021/011256.

*Primary Examiner* — Mohammed Rachedine
(74) *Attorney, Agent, or Firm* — Scully, Scott, Murphy & Presser, P.C.

(57) ABSTRACT

A control apparatus includes a processor to control transmission/reception, a transmission/reception unit configured to transmit/receive wireless signals from a plurality of transmitting antennas using a plurality of receiving antennas that can transmit/receive the signals, a first sensitivity acquisition unit configured to acquire a first communication sensitivity of a first receiving antenna that receives main signals from the first transmitting antenna, and a second sensitivity acquisition unit configured to acquire second communication sensitivities of a plurality of antenna pairs each made up of any one of the plurality of transmitting antennas and any one of the plurality of receiving antennas for transmitting/receiving sub-signals, in which the plurality of receiving antennas are arranged at predetermined relative angles, and the second sensitivity acquisition unit calculates communication sensitivities of all the plurality of receiving antennas based on some of communication sensitivities of the plurality of receiving antennas.

16 Claims, 6 Drawing Sheets

(52) U.S. Cl.
    CPC ....... *A61B 1/00055* (2013.01); *H04B 7/0608*
               (2013.01); *H04B 7/0802* (2013.01)

(56)           References Cited

U.S. PATENT DOCUMENTS

| | | | |
|---|---|---|---|
| 2011/0299616 A1* | 12/2011 | Ma ........................ | H04B 7/0665 |
| | | | 375/267 |
| 2021/0076916 A1* | 3/2021 | Ming ..................... | A61B 1/045 |
| 2022/0218181 A1* | 7/2022 | Koide .................... | A61B 1/041 |

FOREIGN PATENT DOCUMENTS

| | | | | |
|---|---|---|---|---|
| JP | 2010-207459 A | 9/2010 | | |
| JP | 5464817 B2 | 4/2014 | | |
| JP | 2016-159021 A | 9/2016 | | |
| JP | 2020-156037 A | 9/2020 | | |
| WO | WO-2005074785 A1 * | 8/2005 | ......... | A61B 1/00016 |
| WO | WO-2020157909 A1 * | 8/2020 | ......... | A61B 1/00009 |

\* cited by examiner

FIG. 2

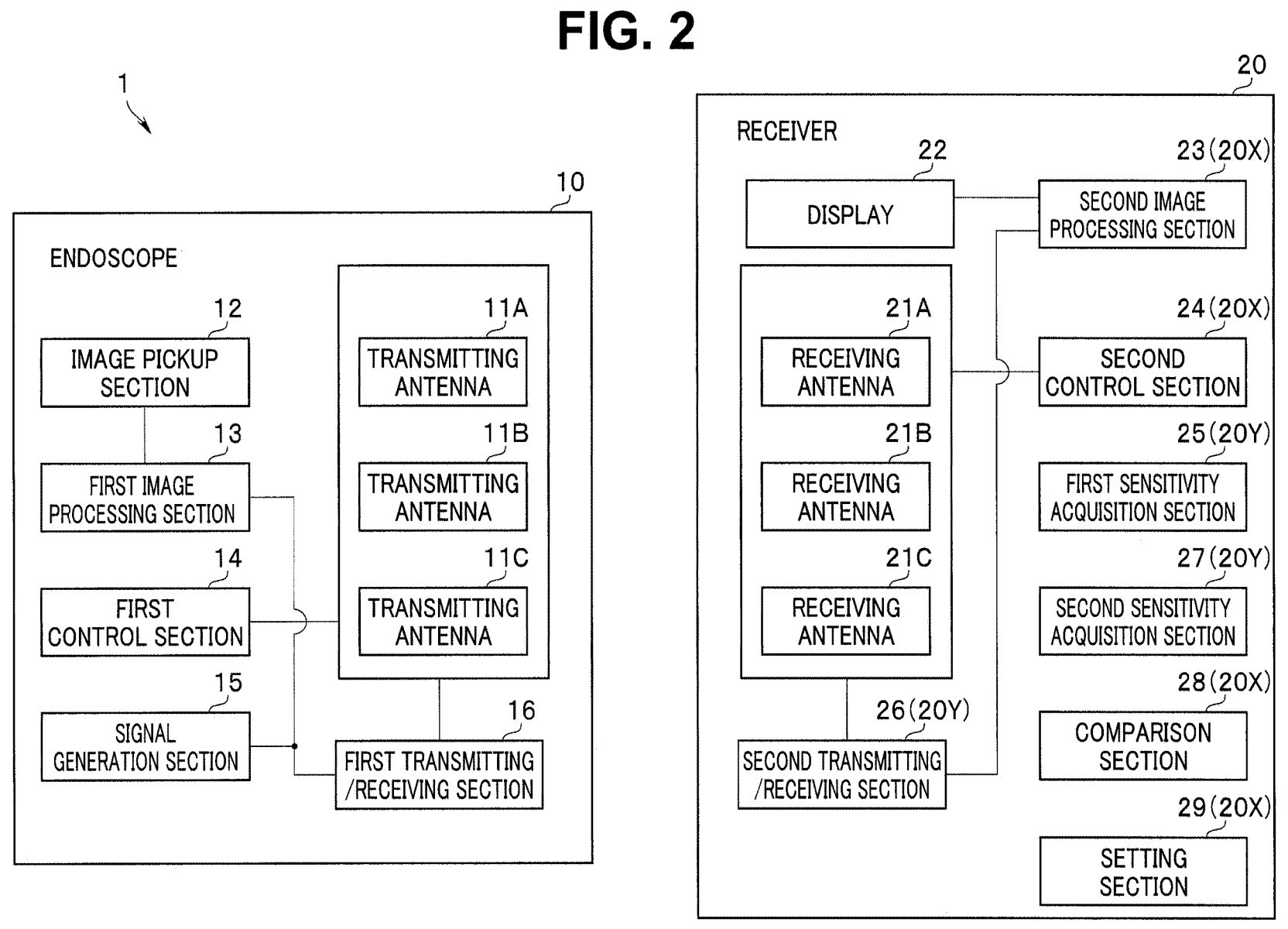

RECEIVER 20

23 (20X) SECOND IMAGE PROCESSING SECTION 24 (20X) SECOND CONTROL SECTION 25 (20Y) FIRST SENSITIVITY ACQUISITION SECTION 27 (20Y) SECOND SENSITIVITY ACQUISITION SECTION 28 (20X) COMPARISON SECTION 29 (20X) SETTING SECTION

22 DISPLAY

21A RECEIVING ANTENNA

21B RECEIVING ANTENNA

21C RECEIVING ANTENNA 26 (20Y) SECOND TRANSMITTING /RECEIVING SECTION

ENDOSCOPE 10

11A TRANSMITTING ANTENNA

11B TRANSMITTING ANTENNA

11C TRANSMITTING ANTENNA

16 FIRST TRANSMITTING /RECEIVING SECTION

12 IMAGE PICKUP SECTION

13 FIRST IMAGE PROCESSING SECTION

14 FIRST CONTROL SECTION

15 SIGNAL GENERATION SECTION

1

CONTROL APPARATUS, MEDICAL SYSTEM AND METHOD FOR OPERATING MEDICAL SYSTEM

CROSS REFERENCE TO RELATED APPLICATION

This application is a continuation application of PCT/JP2021/011256 filed on Mar. 18, 2021, the entire contents of which are incorporated herein by this reference.

BACKGROUND OF THE INVENTION

1. Field of the Invention

An embodiment of the invention relates to a control apparatus of a medical system that transmits/receives wireless signals, a medical system that transmits/receives wireless signals and a method for operating a medical system that transmits/receives wireless signals.

2. Description of the Related Art

Endoscope systems for observing inside body cavities or the like of patients are widely used. Endoscope images are transmitted via a cable from an endoscope to a processor that performs signal processing.

Japanese Patent Application Laid-Open Publication No. 2016-159021 describes the development of a wireless endoscope that includes a rechargeable battery and transmits endoscope images as wireless signals to a processor. In an endoscope system including the wireless endoscope, wireless signals transmitted from a transmitting antenna of the endoscope are received by a receiving antenna of the processor. The wireless endoscope without any cables has good operability.

SUMMARY OF THE INVENTION

A control apparatus according to an embodiment of the invention is a control apparatus including a processor configured to control transmission/reception using a plurality of receiving antennas including a first receiving antenna and a second receiving antenna, the control apparatus including a transmission/reception unit configured to transmit/receive wireless signals from a plurality of transmitting antennas including a first transmitting antenna and a second transmitting antenna using the plurality of receiving antennas, each of which can transmit/receive the wireless signals, a first sensitivity acquisition unit configured to acquire a first communication sensitivity of the first receiving antenna that receives main signals of the wireless signals from the first transmitting antenna, and a second sensitivity acquisition unit configured to acquire second communication sensitivities of a plurality of antenna pairs each made up of any one of the plurality of transmitting antennas and any one of the plurality of receiving antennas for transmitting/receiving sub-signals of the wireless signals, in which the plurality of receiving antennas are arranged at predetermined relative angles, the second sensitivity acquisition unit calculates communication sensitivities of all the plurality of receiving antennas based on some of communication sensitivities of the plurality of receiving antennas, and when a highest communication sensitivity between the second transmitting antenna and the second receiving antenna among the second communication sensitivities is higher than the first communication sensitivity, the processor sets an antenna pair made up of the second transmitting antenna and the second receiving antenna as an antenna pair transmitting; receiving the main signals.

A method for operating a medical system according to the embodiment of the invention, the method including acquiring a first communication sensitivity of an antenna pair comprising a first transmitting antenna and a first receiving antenna transmitting/receiving main signals of wireless signals, a plurality of transmitting antennas including the first transmitting antenna and a second transmitting antenna, each of which can transmit/receive wireless signals, and a plurality of receiving antennas including the first receiving antenna and a second receiving antenna, each of which can transmit/receive the wireless signals, acquiring second communication sensitivities of a plurality of antenna pairs each made up of any one of the plurality of transmitting antennas and any one of the plurality of receiving antennas for transmitting/receiving sub-signals of the wireless signals, and when a highest communication sensitivity between the second transmitting antenna and the second receiving antenna among the second communication sensitivities is higher than the first communication sensitivity, setting an antenna pair made up of the second transmitting antenna and the second receiving antenna as a first antenna pair transmitting/receiving the main signals.

A medical system according to the embodiment of the invention includes a plurality of transmitting antennas including a first transmitting antenna and a second transmitting antenna, each of which can transmit/receive wireless signals, a plurality of receiving antennas including a first receiving antenna and a second receiving antenna, each of which can transmit/receive the wireless signals, a first sensitivity acquisition unit configured to acquire a first communication sensitivity of an antenna pair made up of the first transmitting antenna and the first receiving antenna for transmitting/receives main signals of the wireless signals, a second sensitivity acquisition unit configured to acquire second communication sensitivities of a plurality of antenna pairs each made up of any one of the plurality of transmitting antennas and any one of the plurality of receiving antennas for transmitting/receiving sub-signals of the wireless signals, and a setting unit configured to set, when a highest communication sensitivity between the second transmitting antenna and the second receiving antenna among the second communication sensitivities is higher than the first communication sensitivity, an antenna pair made up of the second transmitting antenna and the second receiving antenna as an antenna pair transmitting/receiving the main signals.

BRIEF DESCRIPTION OF THE DRAWINGS

FIG. 2 is a configuration diagram of the medical system according to the embodiment;

DETAILED DESCRIPTION OF THE PREFERRED EMBODIMENT

<Endoscope System>

Figure 1:
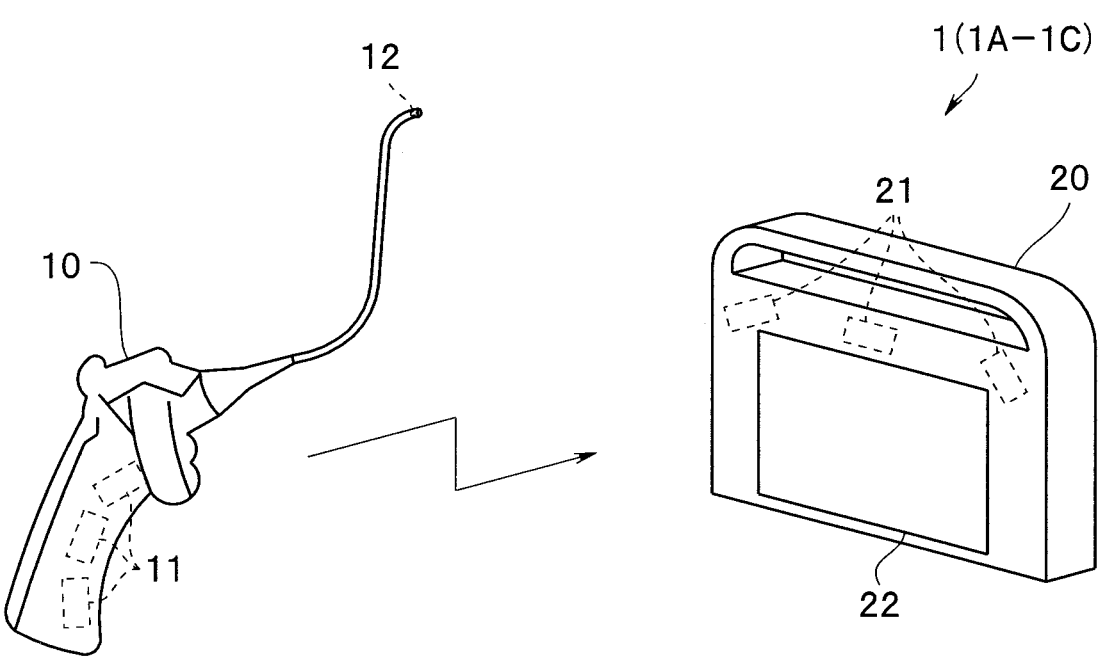
FIG. 1 is an outline view of a medical system according to an embodiment.

An endoscope system 1, a medical system according to an embodiment shown in FIG. 1 and FIG. 2, is equipped with a wireless endoscope 10 (hereinafter referred to as an "endoscope 10") and a receiver 20. The wireless endoscope 10 includes an image pickup section 12 at a distal end portion of an elongated insertion portion, for example. The receiver 20, a portable monitor, includes a display 22 configured to display endoscope images. Hereinafter, a configuration related to wireless communications of the endoscope system 1 will be described.

Note that drawings in the embodiment or the like are schematic views, A relationship between the thickness and width of each component and a ratio of thickness of each component or the like among the respective components are different from the actual relationship and thickness ratio. The drawings include parts whose dimensional relationships and ratios are different among the drawings. Schematic representations and assignment of reference numerals of some components are omitted.

Wireless communications in, for example, a 5-GHz band or 60-GHz band are carried out between the transmitting antennas 11 of the wireless endoscope 10 and the receiving antennas 21 of the receiver 20.

Note that as will be described later, the transmitting antennas 11 can not only transmit but also receive wireless signals. The receiving antennas 21 can not only receive hut also transmit wireless signals. However, for convenience, endoscope antennas transmitting image signals, main signals, are called the "transmitting antennas 11" and receiver antennas receiving image signals are called the "receiving antennas 21."

Since the receiver 20 has a built-in battery as in the case of the wireless endoscope 10, the receiver 20 can be easily carried around.

The configuration of the endoscope system 1 will be described using FIG. 2.

The endoscope 10 is provided with a plurality of transmitting antennas 11 (11A to 11C), an image pickup section (image pickup unit) 12, a first image processing section (first image processing unit) 13, a first control section (first controller) 14, a signal generation section (signal generation unit) 15, and a first transmitting/receiving section (First transmission/reception unit) 16.

Hereinafter, when each of a plurality of components is referred to, one alphabetic character at the end is omitted. For example, each of the transmitting antennas 11A to 11C is called the transmitting antennas 11.

The image pickup section 12 includes an image sensor configured to acquire endoscope images. The first image processing section 13 is configured to perform predetermined image processing such as image compression processing on an endoscope image and output an image signal. The first control section 14 is configured to control overall operation of the endoscope 10 and control wireless transmission/reception, for example, switching control of the transmitting antennas 11, which will be described later. The signal generation section 15 is configured to generate signals to acquire a second communication sensitivity which will be described later. The First transmitting/receiving section 16 is configured to transmit/receive signals using the transmitting antennas 11.

The receiver 20 is provided with a plurality of receiving antennas 21 (21A to 21C), a display 22, a second image processing section (second image processing unit) 23, a second control section (second controller) 24, a first sensitivity acquisition section (first sensitivity acquisition unit) 25, a second transmitting/receiving section (second transmission/reception unit) 26, a second sensitivity acquisition section (second sensitivity acquisition unit) 27, a comparison section (comparison unit) 28, and a setting section (setting unit) 29. As will be described later, the plurality of receiving antennas 21 are arranged at predetermined relative angles.

The second transmitting/receiving section 26 is configured to transmit receive signals using the receiving antennas 21. The first image processing section 13 is configured to perform predetermined image processing on a received image signal and display the image signal on the display 22. The second control section 24 is configured to control the whole receiver 20 and control wireless transmission/reception, for example, switching control of the receiving antennas 21. As will be described later, the first sensitivity acquisition section 25, the second sensitivity acquisition section 27, the comparison section 28 and the setting section 29 are configured to acquire data to perform switching control of an antenna pair, a combination of the transmitting antennas 11 and the receiving antennas 21.

Note that at least one of the first image processing section 13 or the first control section 14 or the like of the endoscope 10 may be constructed of a first CPU (not shown) operated by software or may be constructed of a dedicated hardware circuit. Moreover, at least one of the second image processing section 23, the second control section 24, the comparison section 28 or the setting section 29 or the like of the receiver 20 may be constructed of a second CPU (not shown) operated by software or may be constructed of a dedicated hardware circuit. Moreover, the software (program) may be stored in a non-transitory computer-readable storage medium and may be read by the CPU and operated.

For example, the second control section 24, the second image processing section 23, the comparison section 28 and the setting section 29 of the receiver 20 constitute a processor 20X which is operated by software. Moreover, the processor the second transmitting/receiving section 26, the first sensitivity acquisition section 25 and the second sensitivity acquisition section 27 constitute a control apparatus 20Y of wireless communication.

The first sensitivity acquisition section 25 is configured to acquire a first communication sensitivity of a first antenna pair made up of a first transmitting antenna and a first receiving antenna that transmits/receives an image signal, a main signal with a largest amount of transmission of wireless signals. The second sensitivity acquisition section 27 acquires second communication sensitivities of a plurality of second antenna pairs made up of any one of the plurality of transmitting antennas and any one of the plurality of receiving antennas, which have not received any main signals, using sub-signals. When a highest communication sensitivity between the second transmitting antenna and the second receiving antenna among the second communication sensitivities is higher than the first communication sensitivity, the setting section 29 sets an antenna pair made up of the second transmitting antenna and the second receiving antenna as the first antenna pair that transmits/receives a main signal.

The endoscope system 1 transmits/receives image signals using the antenna pair with the highest communication sensitivity among the plurality of transmitting/receiving antennas, which prevents communication sensitivity from lowering. The endoscope system 1 can transmit high quality endoscope images even if relative positions between the endoscope 10 and the receiver 20 change or objects interfering with radio wave transmission intrude between the two.

Note that at least any one of the first sensitivity acquisition section 25, the second sensitivity acquisition section 27, the comparison section 28 or the setting section 29 may be a component of the endoscope 10.

<Method for Operating Endoscope System>

Figure 3:
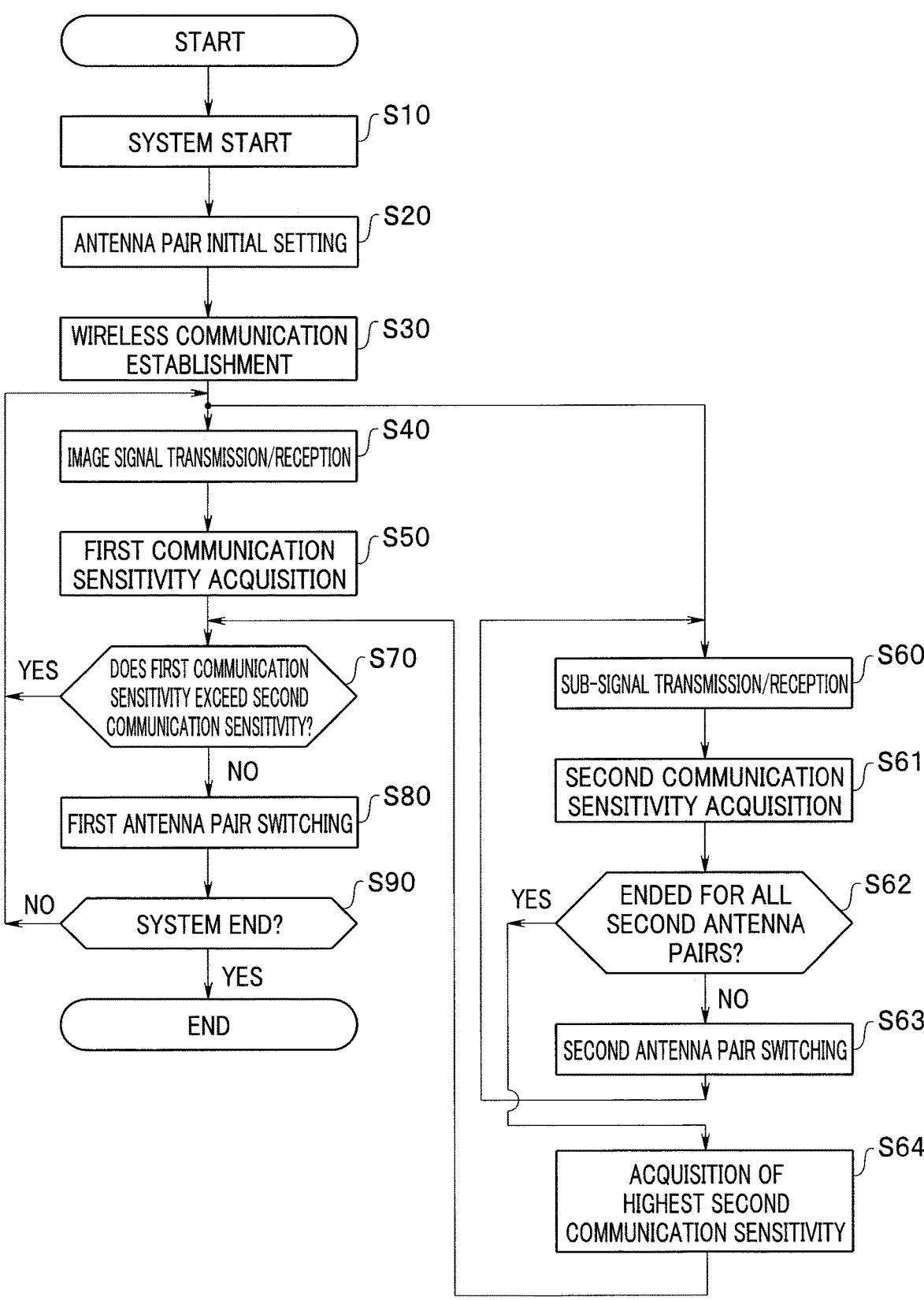
FIG. 3 is a flowchart of operation of the medical system according to the embodiment.

A method for operating the endoscope system 1 will be described according to a flowchart in FIG. 3.

<Step S10> System Start

The endoscope system 1 starts up when the endoscope 10 and the receiver 20 are turned on. The image pickup section 12 of the endoscope 10 starts image pickup and the first image processing section 13 outputs an image signal, a main signal. As will be described later, the signal generation section 15 generates a sub-signal made up of, for example, a sine wave signal with a smaller amount of transmission than an image signal. Note that the signal generation section 15 is not an essential component. For example, a trigger signal used for synchronization control of the image pickup section 12 may be used as a sub-signal to acquire a second communication sensitivity.

<Step S20> Antenna Pair Initial Setting

The setting section 29 sets an antenna pair made up of the transmitting antenna 11A and the receiving antenna 21A as a first antenna pair to be used for transmission/reception of an image signal, a main signal with the largest amount of transmission.

The setting section 29 sets an antenna pair other than the first antenna pair, for example, an antenna pair made up of the receiving antenna 21B and the transmitting antenna 11B as a second antenna pair to be used for transmission/reception of a sub-signal. The sub-signal is a signal other than the main signal and is a signal generated by the signal generation section 15 or an antenna setting signal, which will be described later.

Based on the setting of the setting section 29, the second control section 24 performs switching processing using the receiving antenna 21A as the first receiving antenna that transmits an image signal and using the receiving antenna 21B as the second receiving antenna that transmits/receives a sub-signal.

The setting data of the setting section 29 is wirelessly transmitted from the receiver 20 to the endoscope 10. Based on the setting data of the setting section 29, the first control section 14 performs switching processing using the transmitting antenna 11A as the first transmitting antenna that transmits an image signal and using the transmitting antenna 11B as the second transmitting antenna that transmits a sub-signal.

When the first antenna pair and the second antenna pair at an end of the previous operation are used as they are, no initial setting of the antenna pairs is necessary.

<Step S30> Wireless Communication Establishment

The first transmitting/receiving section 16 of the endoscope 10 and the second transmitting/receiving section 26 of the receiver 20 are paired (wireless communication establishment). There are many wireless devices depending on the place of use. In order to avoid interference and secure necessary bands, the first transmitting/receiving section 16 and the second transmitting/receiving section 26 search for available channels, change the setting if necessary and establish communication. For this reason, pairing may take a long time.

Note that wireless transmission/reception of image signals using the first antenna pair and wireless transmission/reception of sub-signals with a smaller amount of transmission than image signals using an antenna pair other than the first antenna pair can be carried out simultaneously in parallel.

A main signal and a sub-signal may be preferably transmitted/received on different frequencies in order to avoid interference. Sub-signal strength is preferably smaller than main signal strength for low power consumption.

<Step S40> Image Signal Transmission/Reception

The image signal, the main signal outputted from the first transmitting/receiving section 16 of the endoscope 10, is wirelessly transmitted from the transmitting antenna 11A set as the first transmitting antenna. The image signal is received by the receiving antenna 21A set as the first receiving antenna of the receiver 20.

The received image signal is processed 1w the second image processing section 23 and displayed on the display 22.

<Step S50> First Communication Sensitivity Acquisition

The first sensitivity acquisition section 25 acquires a first communication sensitivity, a sensitivity of the image signal received by the second transmitting/receiving section 26. In other words, the first communication sensitivity is a communication sensitivity when a signal is transmitted/received by the first antenna pair. For example, the communication sensitivity is expressed by a ratio of output signal strength to received signal strength. When the main signal strength is the same as the sub-signal strength, the communication sensitivity is expressed by a ratio of received signal strength to noise signal strength.

<Step S60> Sub-Signal Transmission/Reception

The signal generation section 15 generates sub-signals to acquire second communication sensitivities, which are respective communication sensitivities of the plurality of antenna pairs which have not received the main signals. For example, the sub-signal is wirelessly transmitted from the transmitting antenna 11B and received by the receiving antenna 21B of the receiver 20.

<Step S61< Second Communication Sensitivity Acquisition

The second sensitivity acquisition section 27 acquires the second communication sensitivity, the sensitivity of the sub-signal received by the second transmitting/receiving section 26.

<Step S62> End of Acquisition of Second Communication Sensitivities of all Second Antenna Pairs?

The endoscope system 1 has three transmitting antennas 11A to 11C and three receiving antennas 21A to 21C. Of these antennas, the antenna pair made up of the one transmitting antenna 11 and the one receiving antenna 21 is the first antenna pair that transmits/receives the main signal. When a plurality of antenna pairs of all combinations of the two transmitting antennas 11 and the two receiving antennas 21 not set as the first antenna pair are used for transmission, the second communication sensitivities are acquired.

According to the present embodiment, when acquisition of the second communication sensitivity has not been completed for the following four antenna pairs (NO), the process in step S63 is carried out. When the second communication sensitivity acquisition has been completed (YES), the process in step S64 is carried Out.

(Antenna pair A) transmitting antenna 11B/receiving antenna 21B (Antenna pair B) transmitting antenna 11C/receiving antenna 21C (Antenna pair C) transmitting antenna 11B/receiving antenna 21C (Antenna pair D) transmitting antenna 11C/receiving antenna 21B<

Step S63> Second Antenna Pair Switching

The setting is switched to a combination of antenna pairs for which second communication sensitivity acquisition has not been completed. The processes in and after step S60 are carried out again.

<Step S64> Acquisition of Highest Second Communication Sensitivity

The comparison section 28 compares the second communication sensitivities of the four antenna pairs and acquires the highest communication sensitivity. The transmitting antenna of the second antenna pair with the highest communication sensitivity is called a "second transmitting antenna" and the receiving antenna is called a "second receiving antenna."

Note that steps S40 to S50 (first communication sensitivity acquisition process) and steps S60 to S64 (second communication sensitivity acquisition process) are carried out simultaneously in parallel.

<Step S70> First Communication Sensitivity>Second Communication Sensitivity

The comparison section 28 compares the first communication sensitivity with the second communication sensitivity. When the first communication sensitivity exceeds the second communication sensitivity (YES), the processes in and after steps S40 and S60 are carried out. In contrast, when the first communication sensitivity is equal to or lower than the second communication sensitivity (NO), a process in step S80 is carried out.

<Step S80> First Antenna Pair Switching

The antenna pair of the second transmitting antenna and the second receiving antenna, the antenna pair with the highest communication sensitivity, is set by the setting section 29 as a first antenna pair that transmits/receives an image signal.

For example, the antenna pair A (transmitting antenna 11B/receiving antenna 21B) is set as the first antenna pair.

Based on the setting by the setting section 29, the second control section 24 uses the receiving antenna 21B as the first receiving antenna that transmits an image signal.

The setting data of the setting section 29 is wirelessly transmitted from the receiver 20 to the endoscope 10. Based on the setting data of the setting section 29, the first control section 14 uses the transmitting antenna 11B as the first transmitting antenna that transmits image signals.

<Step S90> System End?

The processes in and after steps S40 and S60 are carried out until the operation of the endoscope system 1 is completed (NO).

According to the method for operating the endoscope system 1, image signals are transmitted/received using an antenna pair with the highest communication sensitivity among the plurality of transmitting/receiving antennas, which prevents deterioration of communication sensitivity. According to the method for operating the endoscope system 1, even if relative positions between the endoscope 10 and the receiver 20 change, high quality endoscope images can be transmitted.

Note that the processes from steps S40 to S90 may be carried out continuously or, for example, about once every five seconds.

The endoscope system 1 should have at least two transmitting antennas 11 and at least three receiving antennas 21. For example, the endoscope 10 may have two transmitting antennas 11 and the receiver 20 may have five receiving antennas 21. The receiver 20 can easily place more antennas than the endoscope 10. For this reason, the number of receiving antennas 21 is preferably larger than the number of transmitting antennas 11. The number of transmitting antennas 11 is preferably 2 or more and 5 or less, and the number of receiving antennas 21 is preferably 3 or more and 20 or less. When the number of antennas is larger than or equal to the above-described range, stable transmission/reception is possible. When the number of antennas is less than or equal to the above-described range, it is possible to respond quickly to changes in transmission/reception conditions that may occur.

MODIFICATIONS

An endoscope system 1A according to a modification is similar to the endoscope system 1, and so components with the same functions are given the same reference numerals and description is omitted.

Modification 1

In the endoscope system 1A according to the present modification, when the first communication sensitivity exceeds a predetermined first sensitivity, the second sensitivity acquisition section 27 does not acquire any second communication sensitivity.

Figure 4:
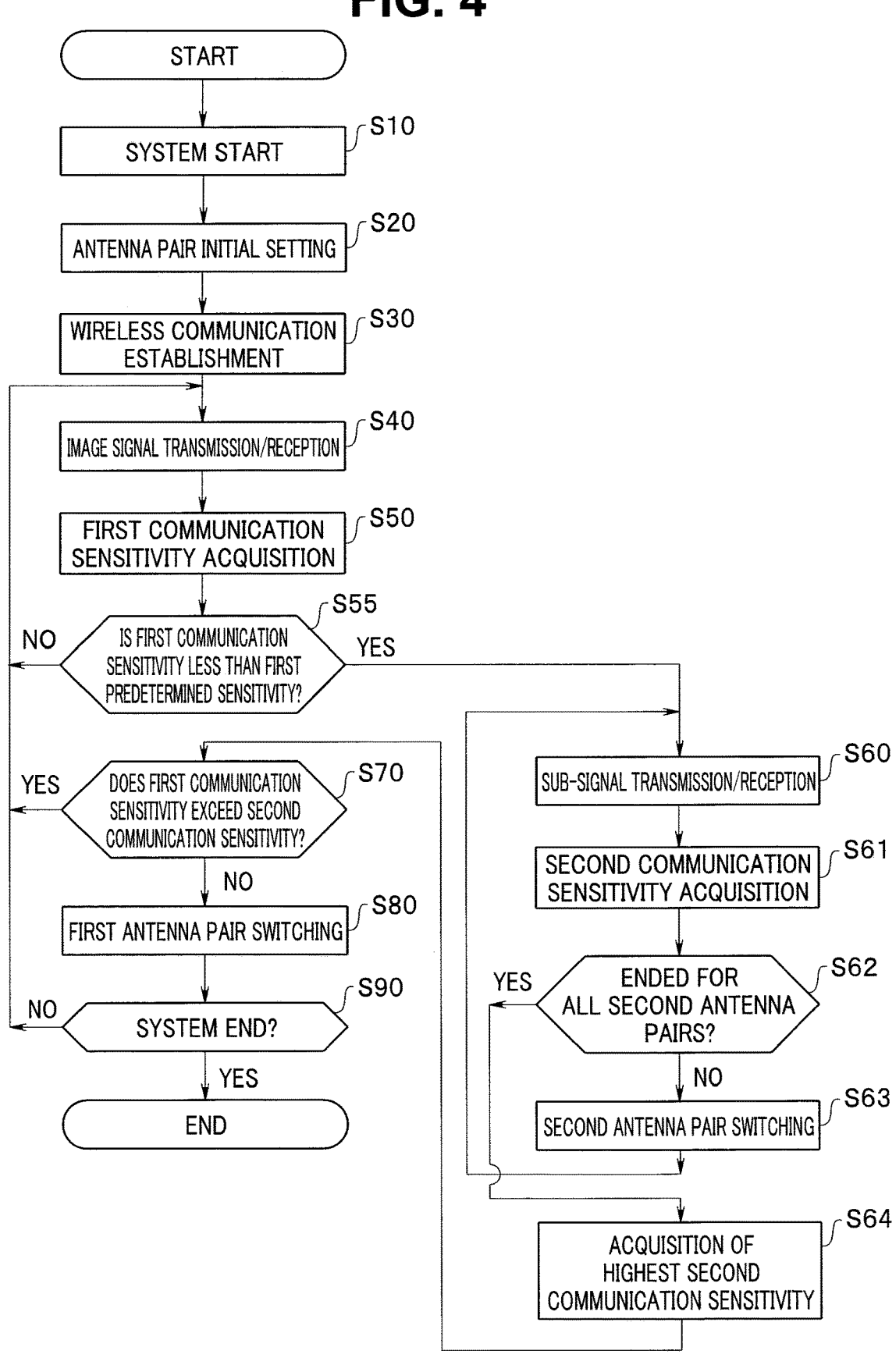
FIG. 4 is a flowchart of operation of a medical system according to modification 1.

Operation of the endoscope system 1A will be described according to a flowchart in FIG. 4.

<Steps S10 to S50>

The steps are the same as steps S10 to S50 of the endoscope system 1, which have already been described.

<Step S55>

The comparison section 28 compares the first communication sensitivity with a first sensitivity. When the first communication sensitivity is equal to or less than the first sensitivity (YES), the same processes as the processes in steps S60 to S90 of the endoscope system 1 are carried out. In contrast, when the first communication sensitivity exceeds the first sensitivity (NO), the processes in steps S60 to S90 for first antenna pair switching are not carried out, but the first communication sensitivity acquisition processes in and after step S40 are carried out. The first sensitivity exceeds 150% of a minimum sensitivity, which may cause interference with transmission of a main signal, for example.

An endoscope system 1A does not carry out any second communication sensitivity acquisition process as long as there is no risk of causing interference with transmission/reception by the first antenna pair. Thus, the endoscope system 1A has effects of the endoscope system 1 and moreover, consumes less power than the endoscope system 1.

Modification 2

When the first communication sensitivity and the second communication sensitivity are less than a predetermined second sensitivity, an endoscope system 1B of the present modification generates an alarm. The second sensitivity is less than, for example, 110% of a minimum sensitivity that may cause interference with transmission of the main signal, Note that the control section configured to generate the alarm may be at least one of the first control section 14 or the second control section 24.

Figure 5:
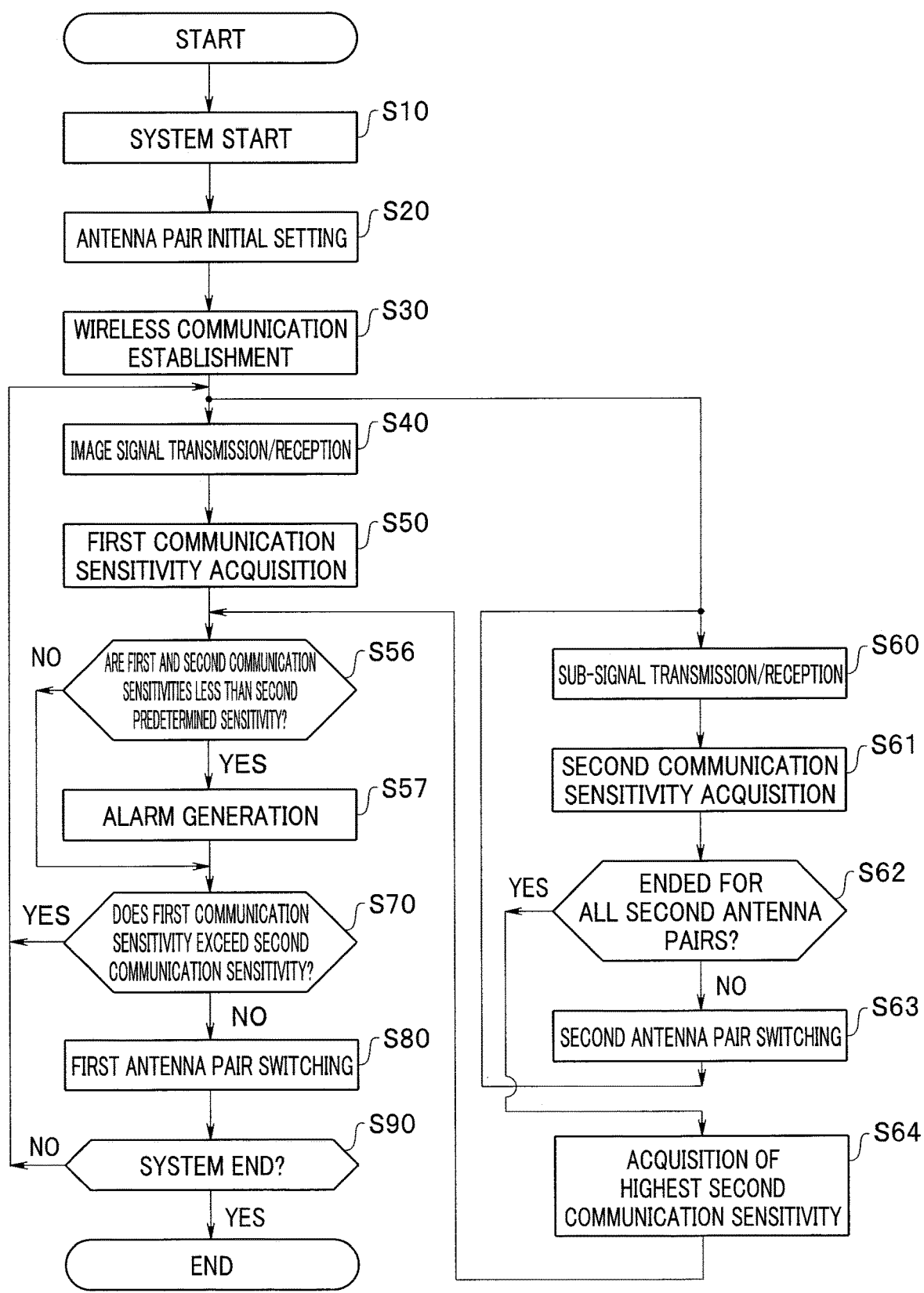
FIG. 5 is a flowchart of operation of a medical system according to modification 2.

Operation of the endoscope system 1B will be described according to a flowchart in FIG. 5.

<Steps S10 to S50>

The steps are the same as steps S10 to S50 of the endoscope system 1, which has already been described.

<Step S56>

The comparison section 28 compares the first communication sensitivity and the second communication sensitivity with the second sensitivity. When the first communication sensitivity and the second communication sensitivity are less than the second sensitivity (YES), for example, at least one of the first control section 14 or the second control section 24 generates an alarm. In contrast, when the first communication sensitivity or the second communication sensitivity are equal to or larger than second sensitivity (NO), the processes in and after step S70 are carried out.

In other words, when transmission/reception is interrupted using any antenna pair, the endoscope system 1B generates an alarm. For this reason, the user can change the way to hold the endoscope or change the arrangement of the receiver 20. The endoscope system 1B has effects of the endoscope system 1 and is less likely to cause interference with wireless communication.

Note that the endoscope system according to the embodiment may have the configuration of the endoscope system 1A or 1B.

Modification 3

In an endoscope system 1C according to the present modification, a plurality of receiving antennas 21 are arranged at predetermined relative angles and the second sensitivity acquisition section 27 calculates communication sensitivities of all the plurality of receiving antennas based on communication sensitivities of some of the plurality of receiving antennas.

Figure 6:
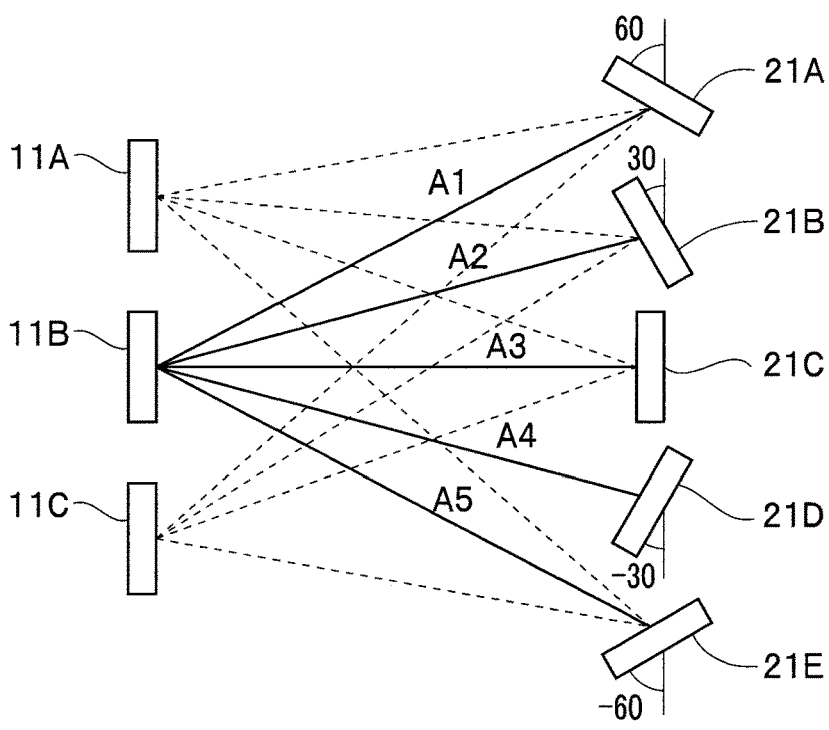
FIG. 6 is a diagram illustrating an antenna pair of a medical system according to modification 3.

As shown in FIG. 6, the endoscope system 1C has three transmitting antennas 11A to II C and five receiving antennas 21A to 21E, The five receiving antennas 21A to 21E are arranged at predetermined relative angles. For example, the receiving antenna 21A is inclined 60 degrees with respect to the receiving antenna 21C and the receiving antenna 21B is inclined 30 degrees.

Figure 7:
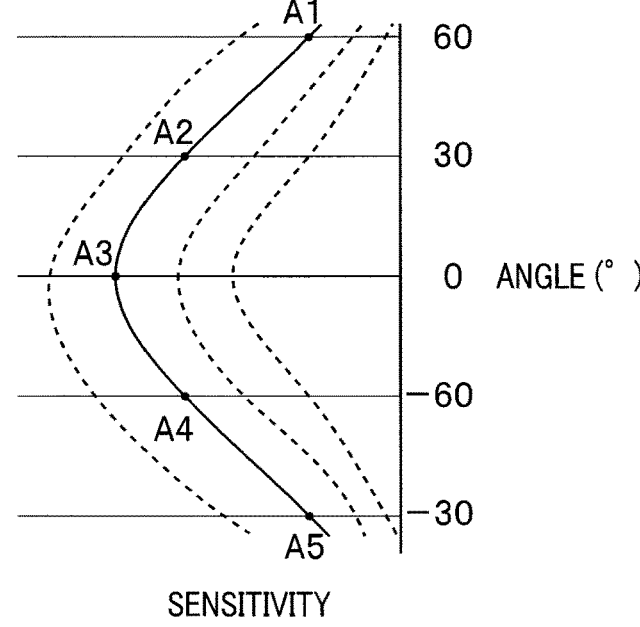
FIG. 7 is a diagram illustrating sensitivity of the antenna pair according to modification 3.

FIG. 7 shows communication sensitivities A1 to A5 when a signal transmitted by the transmitting antenna 11B is received by the five receiving antennas 21A to 21E. Shapes of communication sensitivity curves connecting the transmitting antenna 11B and communication sensitivities A1 to A5 of the receiving antennas 21A to 21E can be acquired theoretically or experimentally in advance.

For this reason, the second sensitivity acquisition section 27 can calculate communication sensitivities of all the receiving antennas based on communication sensitivities of some of the receiving antennas 21.

For example, it is possible to calculate communication sensitivities A2, A3 and A5 by acquiring the communication sensitivity A1 of the receiving antenna 21A and the communication sensitivity A4 of the receiving antenna 21D and causing the communication sensitivities A1 and A4 to be curve fitted to a pre-recorded curve.

Effects of the endoscope system 1C are noticeable when the number of receiving antennas 21 is 4 or more. The number of receiving antennas 21 for which communication sensitivities are actually measured may be preferably 30% or more or particularly preferably 60% or more of the number of receiving antennas 21 provided to ensure predetermined accuracy.

Note that when curve fitting accuracy is poor, for example, when a communication sensitivity AX of a receiving antenna 21X is deviating significantly from the fitting curve, it is preferable to acquire a communication sensitivity AY of a receiving antenna 21Y for which communication sensitivity has not been acquired. The communication sensitivity AY is used instead of the communication sensitivity AX together with communication sensitivity of the acquired receiving antenna and subjected to curve fitting again. Alternatively, communication sensitivities of a plurality of unacquired receiving antennas may be newly acquired, used together with communication sensitivities of the acquired receiving antennas, and subjected to curve fitting.

The endoscope system 1C has effects of the endoscope system 1, furthermore consumes less power and can respond quickly to changes in communication conditions.

The endoscope system 1C may have the configuration of at least one of the endoscope system 1A or 1B.

At least any one of the first sensitivity acquisition section 25, the second sensitivity acquisition section 27, the comparison section 28 or the setting section 29 may be a component of the endoscope 10 instead of the receiver 20.

Although an endoscope system has been taken as an example of and for explanation of the medical system, the medical system of the invention may be a treatment instrument system or the like equipped with, for example, a wireless treatment instrument or a wireless ultrasound apparatus.

The endoscope 10 may be a flexible endoscope with a flexible insertion portion or a rigid endoscope with a rigid insertion portion. The endoscope 10 can be used for medical or industrial applications.

The invention is not limited to the aforementioned embodiment or the like, and various modifications and alterations or the like may be made to the invention without changing the gist.

What is claimed is:

1. A control apparatus comprising:

a processor, the processor comprising hardware, the processor being configured to:

control transmission/reception of wireless signals using a plurality of receiving antennas including a first receiving antenna and a second receiving antenna;

transmit/receive the wireless signals from a plurality of transmitting antennas including a first transmitting antenna and a second transmitting antenna using the plurality of receiving antennas, each of which can transmit/receive the wireless signals;

acquire a first communication sensitivity of the first receiving antenna that receives main signals of the wireless signals from the first transmitting antenna;

acquire second communication sensitivities of a plurality of antenna pairs each made up of any one of the plurality of transmitting antennas and any one of the plurality of receiving antennas for transmitting/receiving sub-signals of the wireless signals, wherein the plurality of receiving antennas are arranged at predetermined relative angles;

calculate communication sensitivities of all the plurality of receiving antennas based on some of communication sensitivities of the plurality of receiving antennas;

when the first communication sensitivity and the second communication sensitivities are less than a predetermined second sensitivity, generate an alarm;

when a highest communication sensitivity between the second transmitting antenna and the second receiving antenna among the second communication sensitivities is higher than the first communication sensitivity, set an antenna pair made up of the second transmitting antenna and the second receiving antenna as an antenna pair transmitting/receiving the main signals; and generate, at an antenna pair other than the antenna pair transmitting/receiving the main signals, sub-signals for measuring the second communication sensitivities, the sub-signals being transmitted in parallel with the main signals and having a smaller amount of transmission than the main signals.

2. The control apparatus according to claim 1, wherein the sub-signals are transmitted on a frequency different from a frequency of the main signals, and a strength of the sub-signals is less than a strength of the main signals.

3. The control apparatus according to claim 1, wherein when the first communication sensitivity exceeds a predetermined first sensitivity, the second communication sensitivities are not acquired.

4. The control apparatus according to claim 1, wherein the second communication sensitivities are less than 110% of a minimum communication sensitivity that causes interference with transmission of the main signals.

5. The control apparatus according to claim 1, wherein the main signals are image signals acquired by an image pickup section of a wireless endoscope.

6. A method for operating a medical system, the method comprising:

acquiring a first communication sensitivity of an antenna pair comprising a first transmitting antenna and a first receiving antenna transmitting/receiving main signals of wireless signals, a plurality of transmitting antennas including the first transmitting antenna and a second transmitting antenna, each of which can transmit/receive wireless signals, and a plurality of receiving antennas including the first receiving antenna and a second receiving antenna, each of which can transmit/receive the wireless signals;

acquiring second communication sensitivities of a plurality of antenna pairs each made up of any one of the plurality of transmitting antennas and any one of the plurality of receiving antennas for transmitting/receiving sub-signals of the wireless signals, wherein the plurality of receiving antennas are arranged at predetermined relative angles;

calculating communication sensitivities of all the plurality of receiving antennas based on some of communication sensitivities of the plurality of receiving antennas;

when the first communication sensitivity and the second communication sensitivities are less than a predetermined second sensitivity, generate an alarm;

when a highest communication sensitivity between the second transmitting antenna and the second receiving antenna among the second communication sensitivities is higher than the first communication sensitivity, setting an antenna pair made up of the second transmitting antenna and the second receiving antenna as a first antenna pair transmitting/receiving the main signals; and generating, at an antenna pair other than the antenna pair transmitting/receiving the main signals, sub-signals for measuring the second communication sensitivities, the sub-signals being transmitted in parallel with the main signals and having a smaller amount of transmission than the main signals.

7. The method for operating the medical system according to claim 6, wherein the sub-signals are transmitted on a frequency different from a frequency of the main signals, and a strength of the sub-signals is less than a strength of the main signals.

8. The method for operating the medical system according to claim 6, the method further comprising:

not acquiring the second communication sensitivities when the first communication sensitivity exceeds a predetermined first sensitivity.

9. The method for operating the medical system according to claim 6, wherein the second communication sensitivities are less than 110% of a minimum communication sensitivity that causes interference with transmission of the main signals.

10. The method for operating the medical system according to claim 6, wherein the main signals are image signals acquired by an image pickup section of a wireless endoscope.

11. A medical system comprising:

a plurality of transmitting antennas including a first transmitting antenna and a second transmitting antenna, each of which can transmit/receive wireless signals;

a plurality of receiving antennas including a first receiving antenna and a second receiving antenna, each of which can transmit/receive the wireless signals; and a processor comprising hardware, wherein the processor is configured to:

control transmission/reception of the wireless signals using the plurality of receiving antennas and the plurality of transmitting antennas, acquire a first communication sensitivity of an antenna pair made up of the first transmitting antenna and the first receiving antenna for transmitting/receives main signals of the wireless signals, acquire second communication sensitivities of a plurality of antenna pairs each made up of any one of the plurality of transmitting antennas and any one of the plurality of receiving antennas for transmitting/receiving sub-signals of the wireless signals, when the first communication sensitivity and the second communication sensitivities are less than a predetermined second sensitivity, generate an alarm, set, when a highest communication sensitivity between the second transmitting antenna and the second receiving antenna among the second communication sensitivities is higher than the first communication sensitivity, an antenna pair made up of the second transmitting antenna and the second receiving antenna as an antenna pair transmitting/receiving the main signals; and generate, at an antenna pair other than the antenna pair transmitting/receiving the main signals, sub-signals for measuring the second communication sensitivities, the sub-signals being transmitted in parallel with the main signals and having a smaller amount of transmission than the main signals.

12. The medical system according to claim 11, wherein the sub-signals are transmitted on a frequency different from a frequency of the main signals, and a strength of the sub-signals is less than a strength of the main signals.

13. The medical system according to claim 11, wherein when the first communication sensitivity exceeds a predetermined first sensitivity, the second communication sensitivities are not acquired.

14. The medical system according to claim 11, wherein the plurality of receiving antennas are arranged at predetermined relative angles, and the processor is further configured to calculate communication sensitivities of all the plurality of receiving antennas based on some of communication sensitivities of the plurality of receiving antennas.

15. The medical system according to claim 11, wherein the second communication sensitivities are less than 110% of a minimum communication sensitivity that causes interference with transmission of the main signals.

16. The medical system according to claim 11, wherein the main signals are image signals acquired by an image pickup section of a wireless endoscope.

* * * * *